United States Patent [19]
Fitt et al.

[11] Patent Number: 5,385,608
[45] Date of Patent: Jan. 31, 1995

[54] ABSORBABLE DUSTING POWDER DERIVED FROM REDUCED-PROTEIN MODIFIED STARCH

[75] Inventors: Larry E. Fitt, Orland Park; Harry T. McNary, Westmont, both of Ill.

[73] Assignee: CPC International Inc., Englewood Cliffs, N.J.

[21] Appl. No.: 242,816

[22] Filed: May 16, 1994

Related U.S. Application Data

[60] Division of Ser. No. 862,774, Apr. 3, 1992, Pat. No. 5,346,892, which is a continuation-in-part of Ser. No. 623,158, Dec. 5, 1990, Pat. No. 5,126,334.

[51] Int. Cl.⁶ .................. C08B 31/18; C08B 30/04
[52] U.S. Cl. .................. 106/210; 127/71; 536/102; 536/105; 536/106
[58] Field of Search ............ 127/71; 106/210; 536/102, 105, 106; 514/60; 2/168; 604/292, 265

[56] References Cited

U.S. PATENT DOCUMENTS

| | | | |
|---|---|---|---|
| 2,070,576 | 2/1937 | Bochskandl | 127/32 |
| 2,469,957 | 5/1949 | Fenn | 260/209 |
| 2,548,455 | 4/1951 | Walker et al. | 260/233.3 |
| 2,626,257 | 1/1953 | Caldwell et al. | 260/233.3 |
| 2,938,901 | 5/1960 | Kerr et al. | 260/233.5 |
| 2,951,776 | 9/1960 | Scallet et al. | 127/71 |
| 2,989,521 | 6/1961 | Senti et al. | 260/233.3 |
| 4,064,564 | 12/1977 | Casey | 2/168 |
| 4,139,505 | 2/1979 | Rogols et al. | 536/105 |
| 4,152,783 | 5/1979 | Choksi | 2/168 |
| 4,281,111 | 7/1981 | Hunt et al. | 536/106 |
| 4,540,407 | 9/1985 | Dunn | 604/292 |
| 4,562,086 | 12/1985 | Smolka et al. | 426/578 |
| 4,773,902 | 9/1988 | Lentz et al. | 604/265 |
| 4,853,978 | 8/1989 | Stockum | 2/167 |
| 5,126,334 | 6/1992 | Fitt et al. | 514/60 |
| 5,346,892 | 9/1994 | Fitt et al. | 514/60 |

FOREIGN PATENT DOCUMENTS

| | | |
|---|---|---|
| 2604714 | 8/1977 | Germany . |
| 4164089 | 2/1971 | Japan . |
| 1095268 | 12/1967 | United Kingdom . |
| 2043668 | 2/1980 | United Kingdom . |

OTHER PUBLICATIONS

Whistler, Starach: Chemistry and Technology, Second Edition, 1984, p. 324.
B. Scallet and E. Sowell, Production and Use of Hypochlorite-Oxidized Starches, Chapter X.
M. W. Rutenberg, Starch and Its Modifications, Chapter 22.

*Primary Examiner*—David Brunsman
*Attorney, Agent, or Firm*—Brooks Haidt Haffner & Delahunty

[57] ABSTRACT

Absorbable dusting powders suitable for medical, consumer and industrial applications such as lubricating gloves and medical apparatus are prepared by treating starch with a hypochlorite to remove protein and oxidize some of the hydroxyl groups. The modified starch dusting powders are free flowing and are characterized by a protein content of less than about 0.15% by weight and hydroxyl groups oxidized to a level of from about 0.03 to about 0.5% by weight. Protein content can be reduced further by washing with water.

6 Claims, 1 Drawing Sheet

ABSORBABLE DUSTING POWDER DERIVED FROM REDUCED-PROTEIN MODIFIED STARCH

This application is a division of application Ser. No. 07/862,774, now U.S. Pat. No. 5,846,892, filed Apr. 3, 1992, which is a continuation-in-part of application Ser. No. 07/623,158, now U.S. Pat. No. 5,126,334, filed Dec. 5, 1990.

BACKGROUND OF THE INVENTION

1. Field of the Invention

The present invention relates to dusting powders of the type used for lubricating medical apparatus and gloves used in medical, industrial and consumer applications. More particularly, the invention has to do with absorbable dusting powders made from starches having reduced protein content and a low level of carboxyl groups generated through the slight oxidation of hydroxyl groups. For some applications, other hydroxyl groups are cross-linked using a relatively low level of phosphorus oxychloride ($POCl_3$).

2. Description of Related Art

Dusting powders used by the medical profession have been associated with numerous problems. Such powders have traditionally been based on talc. However, it has been discovered that talc causes granulomas in the body. Talc also has come under increasing scrutiny as possibly containing asbestos, a carcinogenic substance. While pure mineral talc is composed of a group of hydrous magnesium silicates, commercial talc has varying compositions depending on the source and method of production. Some of these compositions may be contaminated with asbestos.

Talc has effectively been replaced by starch-based powders, but the starch-based powders have a number of disadvantages too. The use of starch has been associated with peritonitis flowing from the use of corn starch on or in surgeons' gloves and has been associated with infections which occur from glove-borne particles during optical surgery which may cause the cornea to turn opaque. Microbial problems are associated with starch because it is an excellent nutrient medium for virtually all vegetative bacteria such as various pathogenic microorganisms.

Despite the aforementioned disadvantages associated with starch-based powders, they are still used by the medical profession because starch is an inexpensive and readily available raw material. There is a need, therefore, for improved starch dusting powders which overcome many of the foregoing problems.

Starch-based dusting powders which are applied to the surface of surgical gloves and other medical apparatus (e.g. examination gloves, tubing, catheters and drains) which may be exposed to internal parts of the body, such as the peritoneal cavity during surgery, must presently meet strict United States Pharmacopoeia (USP) standards for Absorbable Dusting Powders. These standards are published by the United States Pharmacopeial Convention, Inc., 12601 Twin Brook Parkway, Rockville, Md. 20852 USA. All references to the USP or to USP Standards are to the official standards from Jan. 1, 1990 entitled "USP XXII, NF XVII, The United States Pharmacopeia, The National Formulary." The USP standards presently require cross-linking of the starch to prevent gelatinization which would otherwise occur during sterilization when an autoclave is used. New methods of sterilization employing gamma radiation, however, are expected to bring about changes in the USP requirements.

Epichlorohydrin can be used for cross-linking as disclosed in U.S. Pat. No. 4,853,978 to Stokum. The patent relates to antimicrobial medical gloves which can be coated with epichlorohydrin cross-linked corn starch. The starch serves as an antimicrobial agent and a donning assist. The starch powder is believed to be bioabsorbable if left in a wound site. In some applications, antimicrobials (e.g., compositions having fungicidal, bactericidal and/or bacteriostatic properties) having an affinity for the cross-linked starch can be absorbed on the starch.

When epichlorohydrin is used for cross-linking, there is some risk that residual quantities of toxic chlorohydrins can remain in the product. Thus, alternative types of absorbable dusting powders have been developed. U.S. Pat. No. 4,540,407 to Dunn, for example, discloses the use of a polyol powder which also avoids the problem of starch peritonitis.

A chitin-derived, finely divided biodegradable powder is described in U.S. Pat. No. 4,064,564 to Casey for use as a lubricant on surgical gloves. Derivatized chitin, however, is believed to be expensive relative to modified starch and is difficult to obtain in commercial quantities.

Other medical lubricants are disclosed in U.S. Pat. No. 4,773,902 to Lentz et al. which is directed to the use of oxidized cellulose, and U.S. Pat. No. 4,152,783 to Choski which is directed to a surgeon's glove provided with a sodium bicarbonate powder.

It has now been discovered in accordance with the present invention that a new modified starch having reduced-protein content can be prepared which avoids many of the problems associated with prior art products. The starch is modified by treatment with sodium hypochlorite to remove protein, oxidize some of the hydroxyl groups and whiten the product. The hypochlorite treated starch can be washed with water to reduce residual protein further, and/or it can be washed with pyrogen-free water to reduce pyrogen content (and reduce residual protein further) if desired. As another option, the hypochlorite treated starch, before washing, can be cross-linked with $POCl_3$ at a low level to allow better assimilation while meeting USP Standards. The use of $POCl_3$ for cross-linking avoids any risk of residual chlorohydrins associated with the use of epichlorohydrin.

U.S. Pat. No. 4,562,086 to Smolka et al. discloses a modified starch for use in food applications which is prepared by etherification with an alkylene oxide followed by cross-linking. Phosphorus oxychloride is disclosed as a cross-linking agent. Treatment of corn starch with hypochlorite is disclosed in U.S. Pat. Nos. 2,070,776 to Bochskandl, 2,951,776 to Scallet et al. and 2,989,521 to Serti et al. The Serti et al. patent describes a process whereby starch is first cross-linked with epichlorohydrin followed by treatment with sodium hypochlorite. These patents do not disclose the processing conditions, or the products of the present invention and none of them relate to the preparation of modified starches for medical uses.

SUMMARY OF THE INVENTION

The absorbable dusting powder composition of the invention is made by modifying starch, preferably corn starch, with a hypochlorite to remove most of the protein and oxidize some of the hydroxyl groups. This step also causes whitening of the product. It has been found that protein from plant sources can cause allergenic response in humans. To reduce any possible allergenic reaction from the protein in starch, treatment using hypochlorite is important in the development of an absorbable dusting powder.

In a preferred embodiment of the invention, the hypochlorite treated starch is washed with water to reduce residual protein further and/or it is washed with pyrogen free water to eliminate pyrogens and reduce the microbial load.

The preferred absorbable dusting powder has a relatively neutral pH, from about 5 to about 9, most preferably from about 5.5 to about 8, and causes little or no irritation to the skin. It is physiologically absorbable and therefore is much less likely to cause granulomas, adhesions and other objectionable side effects associated with less absorbable materials presently used in medical applications. The product is compatible with current sterilization techniques utilizing gamma radiation.

In another embodiment of the invention, the hypochlorite treated starch is partially cross-linked with $POCl_3$, before washing with water, to allow better assimilation while meeting present USP standards. A sufficiently low level of cross-linking with $POCl_3$ prevents gelatinization during heat-pressure based sterilization. The low levels of cross-linking also allow favorable assimilation by normal physiological functions. The USP presently requires that sedimentation, a measure which depends on the degree of cross-linking, not exceed a value of 75 milliliters (which, for the product of this embodiment of the present invention, is approximately equivalent to bound phosphorus levels of about 400 parts per million (ppm) as explained later in this specification).

Magnesium oxide (MgO) can be added to the reduced-protein modified starch composition if desired. Magnesium oxide is commonly used to increase the flowability of dry starch products. When the starch materials formulated with magnesium oxide are placed in water, the magnesium oxide becomes magnesium hydroxide, an alkaline substance. The USP has limits on the maximum quantities of magnesium oxide that can be used as well as a maximum pH specification that would be indicative of the generation of magnesium hydroxide in solution.

In addition to medical applications, the starches of the invention can be applied to the surface of gloves used in industrial or consumer applications. As an example of industrial use, gloves employed in clean rooms to make computers, magnetic storage media and chips can be treated with the reduced-protein modified starches.

BRIEF DESCRIPTION OF THE DRAWING

The process sequence for the preferred embodiment of the invention is illustrated in FIG. 1.

FIG. 2 illustrates a starch washing system using three hydroclones. The reacted starch supply is the combined stream from the neutralization stage and the starch recovered from the clarification stage. The product is sent to the dewatering stage.

DETAILED DESCRIPTION OF THE INVENTION

The starting material starch used in accordance with the present invention can be derived from various cereal and root materials including corn, milo, wheat, rice, arrowroot, beet, potato, tapioca, waxy corn and waxy milo. Granular corn starch which is made in the corn wet-milling process is preferred because it is readily available, inexpensive and relatively pure as it is produced so that it does not have to be heavily refined after it comes from a corn-wet milling plant.

Corn starch is a carbohydrate polymer derived from corn of various types and composed of about 25% amylose and 75% amylopectin. It is generally in the form of a fine white powder having a granule size from about 5 to about 25 microns with the average granule size being about 13.9 microns. Bulk density ranges from about 38 to 47 pounds per cubic foot depending on the drying technique used. Flash dried and spray dried starches have bulk densities at the low end of the range and belt dried starches have bulk densities at the high end. Moisture content of corn starch is generally about 12%, but varies with ambient relative humidity. The gelatinization temperature, as defined by the loss of birefringence is from about 68° to 72° C.

The starting material starch can be unmodified or modified. Suitable modified starches include oxidized starches such as those prepared with hypochlorite or peroxide.

The hypochlorite used in accordance with the invention may be a hypochlorite of sodium, potassium, calcium or magnesium. Sodium hypochlorite (NaOCl) is preferred because it is more readily commercially available.

Figure 2:
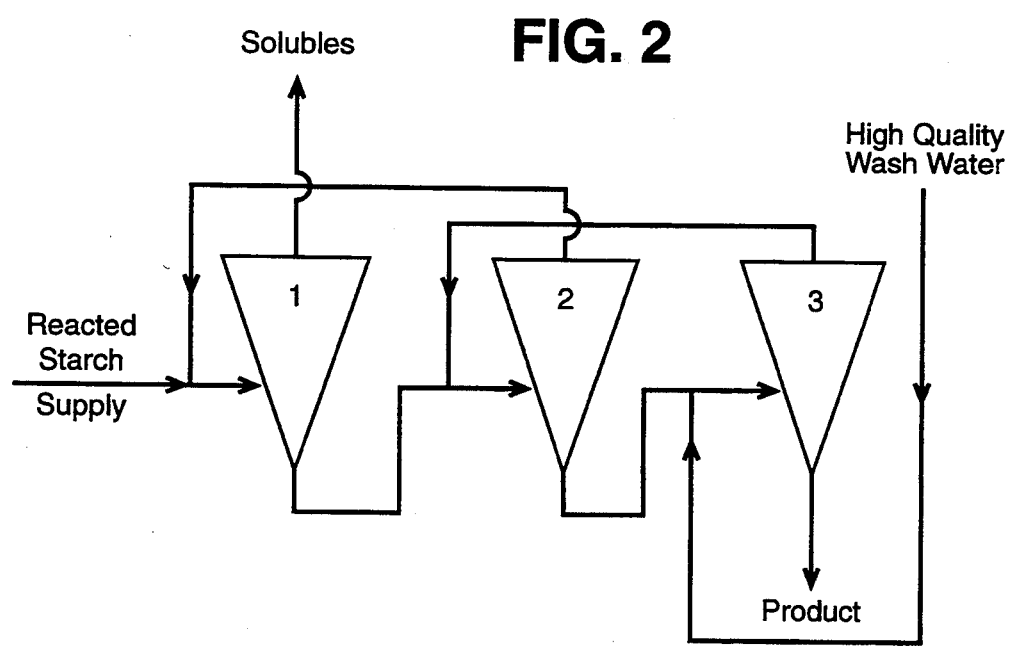
FIG. 2 is a starch washing flow diagram.

Following hypochlorite treatment, the starch can be washed to reduce protein levels further. Washing can be done using conventional equipment such as hydroclones, centrifuges or pressure filters. When hydroclones are used, one can be used, or two or more can be connected in series as illustrated in FIG. 2. It is preferred to use high quality wash water, and pyrogen-free water can be used in one or more of the washing stages to reduce or eliminate pyrogens from the product.

The phosphorus oxychloride ($POCl_3$) which optionally can be used for cross-linking hydroxyl groups in accordance with the invention is a technical grade compound which generally has a specification of 99.5% purity. Phosphorus oxychloride, which is also known as phosphorus oxytrichloride or phosphoryl chloride, is a colorless to pale yellow fuming liquid. It reacts exothermically with water to produce phosphoric and hydrochloric acids. The phosphorus oxychloride treatment step, if it is carried out, takes place following hypochlorite treatment, before washing.

If magnesium oxide is used in accordance with the invention, it should meet the requirements of USP standards.

Figure 1:
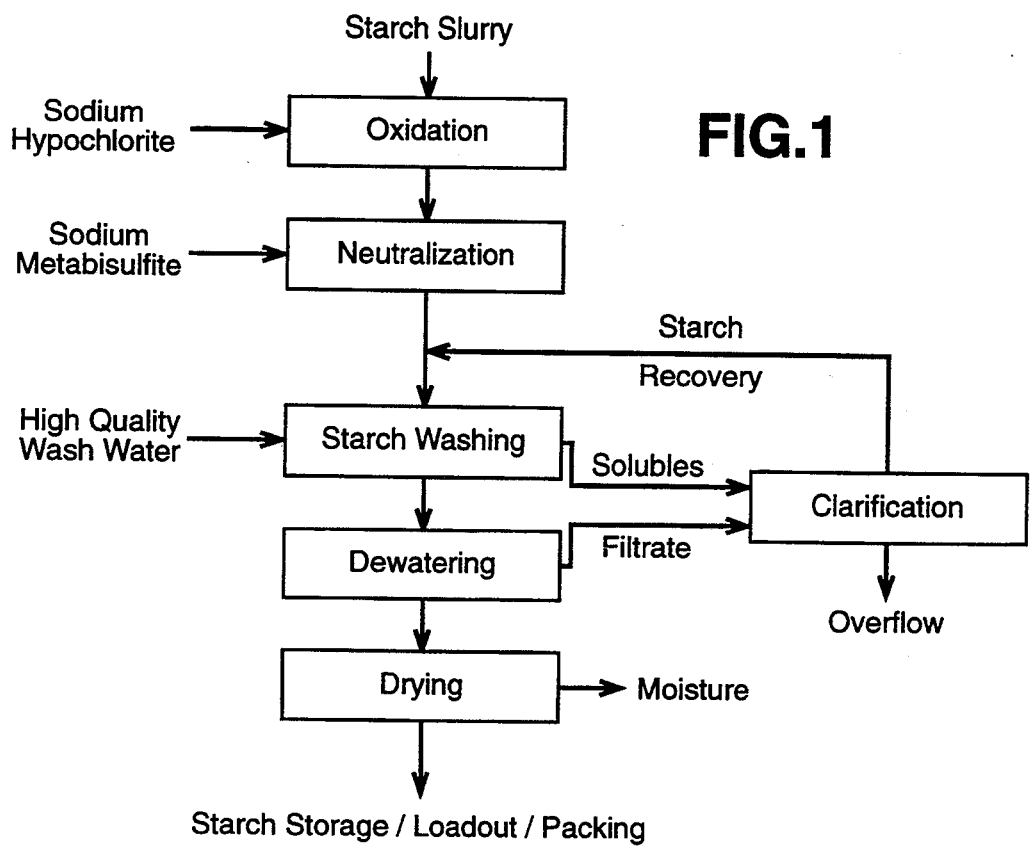
In FIG. 1, a starch slurry is oxidized with sodium hypochlorite followed by neutralization with sodium metabisulfite. High quality wash water, preferably pyrogen free water, is used in a starch washing stage. The underflow from this stage is dewatered and the overflow (solubles) is sent to a clarifier. Dewatered starch is dried and the filtrate from dewatering is sent to the same clarifier as the overflow from starch washing. Starch recovered from the clarifier is recycled to the starch washing stage.

The process of the invention can be carried out in a continuous, semi-continuous or batchwise manner. A continuous process is illustrated in FIG. 1. The first process step comprises treating a slurried starting material starch with a hypochlorite to oxidize some of the hydroxyl groups and remove most of the protein. The slurried starting material starch should have a dry substance (d.s.) from about 10% to about 45%.

The hypochlorite used can have a concentration from about 5% to about 25% by weight (w/w) chlorine. An acid or alkali can be added during or prior to hypochlorite addition to maintain the pH of the reaction mixture at from about 2 to about 10. Suitable reagents for this purpose are hydrochloric acid, sulfuric acid, phosphoric acid, sodium hydroxide and potassium hydroxide.

The starch is preferably reacted with hypochlorite at a temperature from about 100° F. to about 150° F. for a period of time sufficient to remove the protein to a level of less than about 0.15% w/w, with levels of about 0.05% w/w or less being particularly preferred (the objective being to remove as much protein as possible) and oxidize from about 0.03% w/w to about 0.5% w/w of the hydroxyl groups. Typical reaction times are from about 15 minutes to about 2 hours. The degree of oxidation is determined by measuring the carboxyl content of the starch using standard analytical methods such as those set forth in Whistler et al., *STARCH: Chemistry and Technology*, Vol. II (Academic Press 1967) Chapter XXV entitled "Characterization and Analysis of Starches" pp. 620–621; and Bernetti et al., *Modern Methods of Analysis of Food Starches*, Cereal Foods World, Vol. 35 No. 11, November 1990 (American Association of Cereal Chemists Inc. 1990) p. 1102.

Following the reaction with hypochlorite, any free chlorine present in the reaction slurry should be neutralized; otherwise the reaction can continue, even in the dry form, although at a reduced rate. Neutralization, if needed, can be accomplished by admixing a suitable neutralizing compound such as sodium metabisulfite, sodium bisulfite, sodium sulfite, potassium bisulfite, potassium sulfite or sulfur dioxide gas in a sufficient quantity to achieve a value of no detectable chlorine as determined by conventional analytical methods for residual oxidants such as that set forth in the USP Standards for starch, page 1986 [9005-25-8] under "Oxidizing Substances".

At this stage, the reaction slurry can either be directed to the further washing and/or reaction steps, or dewatered and the hypochlorite treated starch can be dried by conventional means and used as a dusting powder or saved for subsequent processing. If the material is to be saved or used as a dusting powder, reaction slurry pH is adjusted to from about 5 to about 9 before dewatering and drying. Suitable pH adjustment agents include sodium hydroxide, potassium hydroxide; hydrochloric, sulfuric or phosphoric acid; or any other acid or base that will yield nontoxic soluble salts. Suitable dewatering techniques include centrifugation and filtration. Drying can be carried out in a flash dryer, ring dryer, spray dryer, belt dryer or the like.

The preferred means of starch slurry washing is with the use of hydroclones. Suitable hydroclones are DORRCLONES, manufactured by Dorr-Oliver Incorporated, 612 Wheeler's Farm Road, Milford, Conn. 06460, U.S.A. Hydroclone washing can be carried out in one stage or, preferably, in several stages in series. FIG. 2 illustrates an embodiment with three hydroclones in series, but more can be used if desired. Solubles are removed in the overflow by concentrating the insoluble material from the supply by a factor of about two in the underflow. The solubles are sent to a clarifier as illustrated in FIG. 1. Suitable clarifiers include membrane filters and diatomaceous earth filters. Centrifuges can also be used for clarification. Suitable centrifuges for use in accordance with this invention are the MERCO centrifuges available from Dorr-Oliver Inc. Dilution for the supply comes from the wash water or, in the case of multi-stage operation, from the overflow from the next hydroclone stage. In FIG. 2, for example, high quality wash water is introduced as the dilution into hydroclone 3, and the overflow from hydroclone 3 is used as the wash water (dilution) for hydroclone 2. The overflow from hydroclone 2 is used as the wash water (dilution) for hydroclone 1. Washed product is taken from the underflow of the hydroclone. In a multi-stage system, washed product is taken from the underflow of the final stage and then is dewatered as illustrated in FIG. 1. Solubles are removed from the overflow of the first stage.

The wash water can be any purified water source. In a preferred embodiment, pyrogen-free water is used which is prepared by passing water through a membrane system. Suitable membranes include those made by Osmonics Inc., Minnetonka, Minn. U.S.A. Pyrogen-free water will have a reduced pyrogen content, the objective being to have little or no detectable pyrogens.

Other washing techniques can be used such as dewatering followed by reslurrying and again dewatering. This can be done in several successive stages if desired. Reslurrying following dewatering should be to about 10 to about 20% w/w solids.

The pH of the washed starch will be more neutral than that of the reacted starch supply, and generally will be from about 6 to about 8.

If the reaction slurry from the hypochlorite treatment stage is subjected to reaction with $POCl_3$, it is adjusted by the addition or removal of water, if necessary, to a d.s. from about 10% to about 45%. If dried hypochlorite treated starch is used, it is reslurried with the addition of water to a d.s. within the same range and mixed to prepare a uniform dispersion. Slurry temperature at this stage is preferably maintained at from about 100° F. to about 150° F.

A salt is added at a level from about 1% to about 5% dry basis (d.b.) to the slurry as a gelation suppressant to reduce the tendency of starch granules to swell in the presence of base or alkali and to retard hydrolysis of the $POCl_3$ reagent. Commonly used salts include sodium chloride and sodium sulfate. Then the pH is adjusted by adding caustic to attain a slurry pH from about 9.0 to about 12.5, preferably from about 11.5 to about 12.5. Suitable caustic agents include sodium hydroxide and potassium hydroxide. Phosphorus oxychloride is then added at a concentration from about 0.05% to about 1.1% w/w, preferably from about 0.5% to about 1.0% w/w, based on dry substance, to cross-link the starch. Typical reaction times are from about 15 to about 45 minutes. At higher slurry temperatures shorter times might be used and longer times may be suitable for lower slurry temperatures. Higher concentrations will result in more cross-linking and lower concentrations will result in less cross-linking.

When the hypochlorite treated starch is reacted with $POCl_3$ the degree of cross-linking of the product of the invention is characterized by bound phosporus levels from about 1200 to about 10 ppm, or less. If it is necessary to meet current USP standards, bound phosphorus should be from about 475 to about 200 ppm and most preferably from about 475 to about 400 ppm. Bound phosphorus levels are determined by standard analytical methods such as published in "Standard Analytical Methods of the Member Companies of the Corn Refiners Association, Inc." Tentative Standard, 10-16-69. pages C-46-1 through C-46-6.

The degree of cross-linking of the $POCl_3$ cross-linked product of the invention can also be expressed as that which will yield a USP sedimentation value in milliliters (ml.) of about 45 to about 100, preferably about 70–95, and most preferably from about 70–75. (The most preferred range is based on present USP standards. However, compositions having higher sedimentation values may be more desirable since they are more easily assimilated by the body.) Excessive cross-linking, yielding a sedimentation value of less than about 45 ml. is detrimental to physiological assimilation which becomes difficult or reduced at such levels.

The $POCl_3$ cross-linked product is then neutralized and washed. Washing can be carried out either before or after neutralizing, but it is preferred to neutralize first because it reduces the presence of ash before washing. (Neutralization is necessary because it converts hydroxides to salts and salts are easier to remove.) Neutralization is accomplished by adding acid to bring the slurry to a pH of from about 6 to about 8. Suitable neutralizing acids include hydrochloric, sulfuric and phosphoric acids. Hydrochloric acid is preferred because it is readily available and essentially all of the resulting salts are soluble. Washing is carried out in the manner described above.

The washed, neutralized slurry is then dried to a moisture content from about 8% to about 14% using a spray dryer, flash dryer, ring dryer, belt dryer or the like.

The dried, reduced-protein, modified starch product is a free flowing white powder and is characterized by a protein content of less than about 0.15%, preferably about 0.05% or less, hydroxyl groups oxidized to a level of from about 0.03% w/w to about 0.5% w/w. When the product is cross-linked with $POCl_3$ it is further characterized by a degree of cross-linking of hydroxyl groups characterized by bound phosphorus levels from about 1200 to about 10 ppm, or less.

The modified starch composition can be used as a medical dusting powder for various applications including surgical gloves, examination gloves, catheters, tubing, drains and the like. It can be admixed with magnesium oxide if desired or if necessary to meet regulatory standards. The magnesium oxide can be added in an amount less than about 2% w/w dry substance and preferably from about 0.5% to about 2% w/w dry substance, with the maximum being based on USP specifications. When magnesium oxide is added, the objective is to obtain an end product having USP sedimentation values within the range of about 45 to about 100 ml., preferably about 70–95 ml. and most preferably about 70–75 ml.

EXAMPLE I

Six samples of absorbable dusting powder were prepared. The final processing steps were conducted in a batch process using a 100 gallon tank provided with an agitator. A high level of agitation was attained by adjusting a portable mixer so that the impeller was near the liquid surface. Agitation was continuous during all of the process steps from preparation of the starch slurry through completion of the cross-linking reaction. Each batch was made in the same way except for variations in concentrations and quantities as indicated below.

Reaction Sequence

One thousand pounds of BUFFALO ® food grade granular starch available from Corn Products, Box 345, Summit-Argo, Ill. 60501 USA, is treated with sodium hypochlorite in a continuous process. The starch is slurried at 41% d.s. and combined with sodium hypochlorite having a concentration of 15% w/w chlorine and 31% w/w hydrochloric acid. The starch slurry is added to a reaction hold tank at a rate of 10.2 liters per minute, sodium hypochlorite is added at a rate of 14.5 liters per hour and hydrochloric acid is added at a rate of 0.69 liters per hour. The reaction mixture in the reaction hold tank is maintained at a temperature of 47° C. (117° F.) and a pH of $6.4\pm0.3$. Residence time in the reaction hold tank is 30 minutes.

Sodium bisulfite (having a concentration of 15% w/w) is admixed with the product leaving the reaction hold tank to neutralize free chlorine. The addition takes place in a neutralization pipeline on the way into a neutralization tank. The flow of sodium bisulfite was adjusted as necessary to achieve no detectable free chlorine.

Soda ash (having a concentration of 5% w/w) is added to the product leaving the neutralization tank. The addition takes place in a neutralization pipeline on the way to a basket centrifuge for dewatering. The flow rate of soda ash is adjusted as necessary to achieve a slurry pH of 5.0–5.5.

The slurry is dewatered in the basket centrifuge and the dewatered hypochlorite-treated starch is dried in a flash dryer to a moisture content of 12% w/w.

Alternatively, one hundred pounds of oxidized starch having a protein content of about 0.15% d.s. is treated with hypochlorite in the same manner as set forth above except that sodium hypochlorite containing about 4% w/w free sodium hydroxide is added at a comparable rate and no hydrochloric acid is added.

For each reaction batch, 45 gallons of water were added to a 100 gallon tank and heated to a temperature of about 110° F. (43° C.) For each of five samples, 300 pounds of the BUFFALO starch (not hypochlorite-treated) was added to prepare starch slurries having 40% starch solids while maintaining the temperature at about 110° F. For the sixth sample, 100 pounds of the hypochlorite-treated BUFFALO starch was added to 30 gallons of water to prepare a starch slurry having 20% starch solids. There was no other adjustment or control of temperature during subsequent processing steps. Each starch slurry was mixed for from about 15 to 30 minutes before further processing. The objective of the mixing was to prepare a uniform dispersion.

Sodium chloride (NaCl) was added to the starch slurry as a dry solid at a level of 3% based on starch dry substance. About 15 minutes after NaCl addition, sodium hydroxide (NaOH) was added as a 4% by weight solution. (The 4% NaOH solution was prepared by adding 50% by weight NaOH to dilution water.) NaOH addition was gradual over a period of about 20 minutes until a concentration of 2.05% by weight NaOH based on starch dry substance was attained. The NaOH addition point was into an area of high agitation on the liquid surface in the reaction tank. Slurry pH after NaOH addition was from about 12.0 to about 12.4.

About 10 minutes after NaOH addition was completed, $POCl_3$ was measured in a graduated cylinder before addition. Of the six samples prepared, two were at a POCl₃ concentration of 0.6% by weight based on starch dry substance, two at 0.8% and two at 1.0%. The concentrations were varied to achieve varying levels of cross-linking. POCl₃ was added gradually over a period of 30–60 seconds. Vapors were controlled with a vent hose connected to an exhaust fan. The cross-linking reaction was considered completed 10 minutes after POCl₃ addition. Reaction slurry pH following cross-linking was from about 11.3 to about 11.9.

Washing and Neutralization

Some of the reaction slurries were separated into two fractions with about one-third being neutralized before washing. The remaining two-thirds were neutralized after washing. Neutralization was accomplished by adding 1% w/w hydrochloric acid to the slurries to bring the pH to about 7.

The cross-linked reaction product was washed in three steps using a 36 inch diameter vacuum nutsche filter. (A nutsche filter is a tank equipped with a false bottom, perforated or porous, that may support a filter medium or may itself act as the septum.) Two different tightly woven filter cloths were used in separate trials. One was a white polyamide-nylon fabric made from a monofilament source having a mesh of -3-53/21 xx and a width of 40-42 inches. This cloth is sold under the trademark MITEX by Tetko Incorporated, 333 S. Highland Avenue, Briarcliff Manor, N.Y. 10523 USA. The other was a gray cotton fabric made from a twisted multifilament thread and sold under the Style Number EMPH 101 by TestFabrics Inc., 200 Blackford Avenue, Middlesex, N.J. 08846 USA. Both filler cloths gave satisfactory results. A vacuum generated by a vacuum pump at a level of 15 inches mercury (Hg) was used. Each filtration cycle was conducted for about 5–15 minutes resulting in filter cakes about 1–3 inches thick having a moisture content of about 50% The filter cakes were reslurried to about 35–40% by weight solids between each step and after the last filtration step.

Drying

The washed, neutralized slurries were each separately spray dried in a DeLaval spray dryer (DeLaval, Inc., Lawrenceville, N.J., USA). Dryer inlet air at a temperature of 300° F. (50° F. wet bulb) was obtained from a gas furnace. Supply slurry was atomized through a high pressure nozzle at 2600 p.s.i.g. at a rate of 15 gallons/hour. Outlet air temperature was controlled at about 150° F. for a target product moisture of 10%. The drying rate was about 50 pounds of product per hour.

The spray dried product was free flowing with low dust generation when handled and had a somewhat granular texture. Microscopic examination revealed roughly spherical agglomerates ranging in size from a few to several hundred individual starch granules. In the presence of water, the agglomerates immediately and totally dispersed.

Product Analyses

Analytical results are summarized in Tables I and II below.

TABLE I

| Sample | POCl₃ dose | % moist. | pH | Ash, % d.b.[1] | Sedimentation[2] |
|---|---|---|---|---|---|
| 1A | 0.6 | 6.7 | 8.9 | 1.6 | 52 |
| 1B | 0.6 | 6.8 | 9.3 | 1.0 | 51 |

TABLE I-continued

| Sample | POCl₃ dose | % moist. | pH | Ash, % d.b.[1] | Sedimentation[2] |
|---|---|---|---|---|---|
| 2A | 0.8 | 7.7 | 9.2 | 1.8 | 47 |
| 2G | 0.8 | 9.9 | 9.3 | 0.7 | 59 |
| 3A[3] | 1.0 | 8.3 | 8.8 | 1.5 | 45 |
| 3B | 1.0 | 10.0 | 9.3 | 1.1 | 50 |

[1] % d.b. means dry basis. Dry basis is calculated by multiplying the sample weight by the dry substance (d.s.) Dry substance is calculated by dividing the dried weight (without moisture) of a sample by the total weight (with moisture) of the sample before drying.
[2] USP Sedimentation in milliliters based on the method associated with the USP specifications.
[3] This sample was tested for heavy metals as representative of the others and 1 ppm heavy metals was detected.

The POCl₃ dose is a percentage based on total starch, dry substance.

The "A" samples and the "G" sample were washed before the neutralization step and the "B" samples were washed after neutralization. The "A" and "B" samples were made using the BUFFALO starch starting material and the "G" sample was made using the hypochlorite-treated BUFFALO starch starting material.

TABLE II

| Sample | Na, ppm d.b. | Protein, % d.b. | Solubles, % d.b. | Bact. | Mold/Yeast |
|---|---|---|---|---|---|
| 1A | 6900 | 0.21 | 1.6 | 3500 | 5 |
| 1B | 2700 | 0.34 | 1.0 | 5200 | 180 |
| 2A | 7000 | 0.20 | 1.9 | 4800 | 70 |
| 2G | 2800 | 0.05 | 1.3 | 7800 | 40 |
| 3A | 4300 | 0.26 | 1.2 | 350 | 10 |
| 3B | 1500 | 0.29 | 0.9 | — | — |

Microbial analyses for bacteria (Bact.) and mold and yeast are in colony forming units per gram (cfu/g).

Sample Formulation with MgO

Each of the six samples was formulated in the laboratory with 0.25, 0.50 and 0.75 percent magnesium oxide to determine the effect on pH and sedimentation volume shown in Table III. A magnesium level of about 0.5% was enough to reach the minimum 10.0 pH for all of the samples and still be within the sedimentation specification.

TABLE III

| | MgO % on d.s. | pH | U.S.P. Sedimentation. ml |
|---|---|---|---|
| 1A | 0 | 8.9 | 52 |
| | 0.25 | 9.65 | 68 |
| | 0.50 | 9.95 | 70 |
| | 0.75 | 10.0 | 70 |
| 1B | 0 | 9.3 | 51 |
| | 0.25 | 9.9 | 58 |
| | 0.50 | 10.05 | 62 |
| | 0.75 | 10.1 | 65 |
| 2A | 0 | 9.2 | 47 |
| | 0.25 | 9.9 | 60 |
| | 0.50 | 10.05 | 63 |
| | 0.75 | 10.2 | 70 |
| 2G | 0 | 9.3 | 59 |
| | 0.25 | 10.2 | 73 |
| | 0.50 | 10.25 | 74 |
| | 0.75 | 10.35 | 76 |
| 3A | 0 | 8.8 | 45 |
| | 0.25 | 10.05 | 60 |
| | 0.50 | 10.2 | 62 |
| | 0.75 | 10.3 | 64 |
| 3B | 0 | 9.3 | 50 |
| | 0.25 | 10.05 | 64 |
| | 0.50 | 10.25 | 66 |
| | 0.75 | 10.3 | 68 |

EXAMPLE II

One hundred pounds of corn starch is slurried at approximately 23° Baume. The pH is adjusted to 2.3 to 2.4 using 75% phosphoric acid. Dilute sodium hypochlorite is added over a period of about 45 minutes to a hypochlorite concentration of about 1.35% w/w based on starch. This produces a starch having a fluidity of about 50 to 70.

After allowing about 20 minutes for reaction, sodium metabisulfite is added to the mixture to neutralize and active chlorine.

Another 20 minutes is allowed for mixing and complete neutralization. Then the starch slurry is checked for free chlorine using o-tuluidine indicator. More sodium metabisulfite is added if the test is positive for free chlorine.

The pH is adjusted to from about 5.0 to about 5.5 using sodium hydroxide.

Excess water is removed and the product is flash dried. Protein in the dried product is less than about 0.1% w/w and carboxyl is below about 0.1% w/w.

The product is washed in four hydroclone stages using pyrogen free water. Then it is flash dried to a moisture content from about 9% to about 12.5% w/w.

Having set forth the general nature and some specific examples of the present invention, the scope is now more specifically set forth in the appended claims.

We claim:

1. A process for preparing a modified starch composition comprising treating a starch with a hypochlorite to remove protein to a level less than about 0.15% by weight and oxidize from about 0.03 to about 0.5% by weight of the hydroxyl groups.

2. The process of claim 1 wherein the hypochlorite is sodium hypochlorite.

3. The process of claim 1 wherein a starch slurry having a dry substance from about 10% to about 45% is first reacted with a hypochlorite at a pH from about 2 to about 10 and a temperature from about 100° to about 150° F. for a period of time sufficient to reduce the protein content of the starch to a level of less than about 0.15% by weight and oxidize from about 0.03 to about 0.5% by weight of the hydroxyl groups.

4. The process of claim 1 wherein the modified starch composition is washed with water to reduce protein content further.

5. The process of claim 4 wherein protein content is reduced to less than about 0.05% by weight.

6. The process of claim 4 wherein the water has been treated to reduce pyrogen content.

* * * * *